(12) United States Patent
Cook et al.

(10) Patent No.: US 7,579,002 B2
(45) Date of Patent: Aug. 25, 2009

(54) METHOD FOR IMPROVING BODY WEIGHT UNIFORMITY AND INCREASING CARCASS YIELD IN ANIMALS

(75) Inventors: Mark E. Cook, Madison, WI (US); Mingder Yang, Madison, WI (US); Kevin Roberson, East Lansing, MI (US)

(73) Assignees: Wisconsin Alumni Research Foundation, Madison, WI (US); Michigan State University, East Lansing, MI (US)

( * ) Notice: Subject to any disclaimer, the term of this patent is extended or adjusted under 35 U.S.C. 154(b) by 496 days.

(21) Appl. No.: 10/761,715

(22) Filed: Jan. 21, 2004

(65) Prior Publication Data
US 2005/0123586 A1    Jun. 9, 2005

Related U.S. Application Data

(60) Provisional application No. 60/527,392, filed on Dec. 5, 2003.

(51) Int. Cl.
*A61K 39/395* (2006.01)

(52) U.S. Cl. .............. 424/157.1; 424/130.1; 424/146.1; 530/388.26; 530/389.1

(58) Field of Classification Search ........................ None
See application file for complete search history.

(56) References Cited

U.S. PATENT DOCUMENTS

| 5,086,067 | A | * | 2/1992 | Djuric et al. | ................. 514/381 |
|---|---|---|---|---|---|
| 5,112,864 | A | * | 5/1992 | Djuric et al. | ................. 514/544 |
| 5,178,873 | A | * | 1/1993 | Horrobin et al. | ............ 424/422 |
| 5,218,124 | A | * | 6/1993 | Failli et al. | ................... 548/180 |
| 6,213,930 | B1 | | 4/2001 | Cook | |
| 6,383,485 | B1 | * | 5/2002 | Cook | ...................... 424/133.1 |
| 2002/0110582 | A1 | | 8/2002 | Place et al. | |
| 2004/0102519 | A1 | | 5/2004 | Llewellyn | |

FOREIGN PATENT DOCUMENTS

| WO | WO 9106537 A2 | * | 5/1991 |
|---|---|---|---|
| WO | WO 9533715 A1 | * | 12/1995 |
| WO | WO 2004/050850 A2 | | 6/2004 |

OTHER PUBLICATIONS

Stryer, L. Biochemistry, 4th edition, W.H. Freeman and Co., 1995, pp. 624-625.*
Granstrom, E. Acta Obstet Gynecol Scand Suppl 1983, 113:9-13.*
Pimentel, J.L., Feedstuffs, 1999, vol. 71, pp. 12-14, 18-19.*
K.D. Croft, et al., Biochimica Et Biophysica Acta, 1985, 834: 316-323, Abstract.
L.J. Machlin, Environmental Quality and Safety. Supplement., 1976, 5: 43-55, Abstract.

* cited by examiner

*Primary Examiner*—Michael Szperka
(74) *Attorney, Agent, or Firm*—Quarles & Brady LLP

(57) ABSTRACT

A method for improving animal body weight uniformity or for increasing animal carcass yield is disclosed. The method involves administering an agent to one or a group of animals wherein the agent can reduce bioavailability of a prostaglandin or leukotriene lipid precursor. In a preferred embodiment, the agent employed is an anti-$PLA_2$ antibody.

8 Claims, No Drawings

METHOD FOR IMPROVING BODY WEIGHT UNIFORMITY AND INCREASING CARCASS YIELD IN ANIMALS

CROSS-REFERENCE TO RELATED APPLICATIONS

This application claims the benefit of U.S. provisional application Ser. No. 60/527,392, filed on Dec. 5, 2003.

STATEMENT REGARDING FEDERALLY SPONSORED RESEARCH OR DEVELOPMENT

This invention was made with United States government support awarded by the following agency: Midwest Poultry Consortium 144-LP69. The United States has certain rights in this invention.

BACKGROUND OF THE INVENTION

The present invention relates to a method of modulating the level of lipid metabolites associated with gastrointestinal inflammation to improve animal body weight uniformity in a group of animals and to increase animal carcass yield.

Body weight uniformity is important to meat-type animals going to slaughter. A high level of body weight uniformity facilitates automation of the slaughtering process and reduces meat processing cost at both the pre-slaughter sorting stage and the slaughter stage. Also, animals raised together often compete with each other for space, feed and water. A more uniform body weight among the animals reduces competition and tends to standardize growth within the group.

Body weight uniformity is also important to groups of animals raised for egg production (e.g., laying hens and duck, turkey and chicken breeders). Peak feed allowance is often provided to a whole group of animals at an estimated egg production stage (e.g., when the whole group reaches 45% egg production). Since egg production age correlates well with body weight, a less uniform body weight for the group means that when peak allowance is provided, the heavy, early maturing animals are close to peak egg production while the smaller immature animals are not yet laying. As a result, the heavy, early maturing animals are underfed and the smaller immature animals are overfed. Improving body weight uniformity will minimize the problem.

Enhancing animal carcass yield is also important to the animal meat industry. Using the poultry industry in the United States as an example, approximately eight billion broilers are raised annually. Therefore, even a slight increase in carcass yield can have a significant economic impact.

Reducing bioavailability of a prostaglandin or leukotriene precursor and thus gastrointestinal inflammation in an animal enhances animal growth and improves feed efficiency. See U.S. Pat. Nos. 6,213,930 and 6,383,485, both incorporated herein by reference in their entirety. However, it is not known or readily predictable whether reducing bioavailability of a prostaglandin or leukotriene precursor can improve animal body weight uniformity or increase animal carcass yield.

Prostaglandins and leukotrienes are lipid metabolites involved in gastrointestinal inflammation. Lipid metabolites isoprostanes may also be involved in gastrointestinal inflammation. Prostaglandins, leukotrienes and isoprostanes can be generated from arachidonic acid in animals. Arachidonic acid is released (as arachidonate) from the sn-2 position of membrane phospholipids by phospholipase $A_2$ ($PLA_2$) and then converted into precursors of biologically active prostaglandins and leukotrienes by lipoxygenase or cyclooxygenase. Since animal feed typically contains a high level of linoleic acid which can be easily converted to arachidonic acid, animals fed with such feed have high levels of prostaglandin and leukotriene precursors ready to be converted to prostaglandins and leukotrienes. Arachidonic acid (released as arachidonate) can also be autooxidized nonenzymatically or oxidized enzymatically into isoprostanes, especially when the activity of lipoxygenase and cyclooxygenase are blocked.

Prostaglandins cause inflammatory effects during gastrointestinal traumas, such as colitis and ulcers, and are involved in vasodilation, vasoconstriction, and stimulation of intestinal or bronchial smooth muscle. Prostaglandins are found in inflammatory exudates and can induce fever and erythema. Leukotrienes cause contraction of smooth muscle, such as intestinal smooth muscle, attract leukocytes and increase vascular permeability. Isoprostanes have vasoconstrictive action on select tissues.

BRIEF SUMMARY OF THE INVENTION

It is disclosed here that animal body weight uniformity, carcass yield, or both can be improved by reducing bioavailability of a prostaglandin, leukotriene or isoprostane lipid precursor in animals. Although it is known in the art that reducing bioavailability of a prostaglandin or leukotriene lipid precursor can enhance animal growth, it is surprising that reducing bioavailability of the precursor can narrow the body weight distribution in a group of animals. Further, it is surprising that reducing bioavailability of a prostaglandin or leukotriene lipid precursor causes a higher percentage of increase in carcass weight than in whole body weight.

In one aspect, the present invention relates to a method for improving animal body weight uniformity among animals in a group of animals. The method involves administering to the animals an agent that can reduce bioavailability of a prostaglandin or leukotriene lipid precursor in the animals in an amount sufficient to improve the body weight uniformity.

In another aspect, the present invention relates to a method for increasing carcass yield of an animal. The method involves administering to the animal an agent that can reduce bioavailability of a prostaglandin or leukotriene lipid precursor in the animal in an amount sufficient to increase carcass yield.

In a preferred embodiment, the agent employed in the above methods is an anti-$PLA_2$ antibody.

It is an object of the present invention to provide a method for improving animal body weight uniformity for a group of animals.

It is another object of the present invention to provide a method for increasing animal carcass yield.

Other objects, advantages and features of the present invention will become apparent from the following specification.

BRIEF DESCRIPTION OF THE SEVERAL VIEWS OF THE DRAWINGS

Not applicable.

DETAILED DESCRIPTION OF THE INVENTION

Body weight uniformity for a group of animals relates to the distribution in the group of body weights relative to the mean body weight. Body weight uniformity can be depicted by a body weight distribution curve with x-axis as body weights and y-axis as the number or percentage of animals within the group. Body weight uniformity can be measured by the variance of the mean body weight, the standard deviation of the mean body weight, the standard error of the mean body weight, the coefficient of variation of the mean body weight and other statistical parameters with which a skilled artisan is familiar. Since the variance, standard deviation and standard error are larger for a group of animals with a higher mean body weight than for a group of animals with a lower mean body weight, even if the body weight distributions of the two groups are the same, the industry has adopted the coefficient of variation as the industry standard to measure body weight uniformity. To determine the coefficient of variation, the standard deviation is normalized by mean body weight [(standard deviation÷mean body weight)×100]. Although for the purpose of the present invention, a decrease in any of the variance, standard deviation, standard error and coefficient of variation of the mean body weight is considered an improvement in body weight uniformity, the coefficient of variation is the preferred parameter for evaluating body weight uniformity. An improvement in body weight uniformity can be assessed by calculating the coefficient of variation of the mean body weight for a group of animals treated with a body-weight-uniformity-improving agent and comparing it to that of the same group of animals before the treatment, to that of a control group of animals as described in Example 1 below, or to any established coefficients of variation available in the art that a skilled artisan deems as an appropriate reference. Preferably, the coefficient of variation is decreased by at least 0.5, and more preferably, by at least 0.8.

The term "carcass yield" is defined here as the carcass weight divided by either the body weight of a live animal immediately before slaughter or the body weight of a dead animal before any body part is separated therefrom. The term carcass is used here to mean a dead animal body after the skin, feathers (if applicable), head, tail (if applicable), feet or extremities, and at least part or all of the viscera are removed, and optionally, after being bled and/or cleared of certain fat tissues (e.g. udders). It is noted here that depending on the animal species and local practice, the exact body parts that are removed can vary and additional tissues such as genital organs may also be removed. The method disclosed here can be practiced with all animals. Preferably the method is practiced on avian animals, mammalian animals or fish. Preferred avian animals include chickens, ducks, turkeys, pheasants, quail, and geese. Preferred mammalian animals include swine animals, bovine animals, ovine animals and caprine animals.

Prostaglandins and leukotrienes are believed to cause gastrointestinal inflammation that increases tissue damage and negatively affects the ability of animals, particularly avians and mammals, to convert feed into body weight. While inflammation negatively affects normal digestion and absorption in the gastrointestinal tract, inflammation also activates the host's immune defense system that demands a supply of nutrients, which are obtained by the body from skeletal muscle via catabolic degradation. By reducing prostaglandin and leukotriene levels and, hence, gastrointestinal inflammation, one body weight-affecting factor that can introduce variance into body weight is attenuated, leading to improved body weight uniformity. Without intending to be limited by theory, the inventors believe that the increase in carcass yield resulting from the reduced prostaglandin and leukotriene levels is due at least in part to the attenuated skeleton muscle degradation.

The inventors have determined that by reducing the available arachidonate, the levels of prostaglandins and leukotrienes are reduced. Therefore, in one embodiment, the present invention is practiced by reducing bioavailability of arachidonate, preferably through preventing arachidonate release from membrane phospholipids. This can be preferably achieved by reducing or eliminating the activity of $PLA_2$, the enzyme that clears arachidonate from membrane phospholipids. The $PLA_2$ activity can be reduced using an anti-$PLA_2$ antibody which, without intending to limit the applicant, is believed to complex with the $PLA_2$ enzyme and thereby interfere with its phospholipase activity.

Polyclonal or monoclonal anti-$PLA_2$ antibodies can be prepared or administered using any of various methods known in the art to produce an antibody or antibody-like factor, including, but not limited to, production in transgenic plants or milk producing animals. Suitable antibodies can be, but need not be separated from non-antibody material. Antibodies are considered suitable in the present method if they are able to reduce $PLA_2$ activity relative to untreated controls in side-by-side in vivo trials.

A skilled artisan can use other methods to reduce $PLA_2$ enzyme activity, such as a method of administering a non-antibody pharmaceutical agent that affects $PLA_2$ activity, in combination with a suitable carrier. One skilled in the art will also appreciate that the method can be practiced by introducing activity-altering changes to the genetic material of animals that encodes the $PLA_2$ enzyme or by interfering with transcription or translation of $PLA_2$. The agent can also limit the availability of a different precursor of prostaglandins or leukotrienes.

The agent can be administered by injection or by oral delivery, and is preferably administered in combination with a suitable carrier of the type commonly used in delivery of pharmaceuticals or nutritional supplements. Injection methods include, but are not limited to, subcutaneous, intraperitoneal, intramuscular, or intravenous injection. Oral administration, which is preferred, can include, but is not limited to, administration in tablet or powder form. Most preferably, the agent is fed directly by mixing with feed or by coating feed particles as described in U.S. Pat. No. 5,725,873, incorporated herein by reference in its entirety.

In a preferred method, antibodies are prepared as follows. A producer animal is immunized with a peptide or protein, such as $PLA_2$, against which antibodies are desired so that the producer animal produces an antibody to said peptide or protein. A substance containing the antibody is obtained from said producer animal. The antibody can be subject to further purification if desired or can be used without further preparation in an animal feed.

The method of Polson, A., M. B. von Wechmar and M. H. van Regenmortel, "Isolation of Viral IgY Antibodies from Yolks of Immunized Hens," Immunological Communications 9:475-493 (1980), incorporated herein by reference in its entirety, can be used to produce a preparation of egg-yolk antibodies. Laying hens can be inoculated with $PLA_2$. Preferably, a suitable adjuvant is administered in conjunction with the hen $PLA_2$ inoculation to enhance the immunization. An adjuvant useful for this purpose is a water-in-oil emulsion adjuvant such as complete Freund's adjuvant. The $PLA_2$ causes the hens to produce anti-$PLA_2$ antibodies which are passively transferred into the egg yolk of eggs laid by the hens.

Egg yolks or whole eggs containing the anti-$PLA_2$ antibody can be collected and homogenized to form an emulsion. The resulting emulsion can be dried to form a powder containing the anti-$PLA_2$ antibody. This powder can then be formulated in a manner appropriate to the administration route and then administered to the desired animals using methods known in the art. The preparation is preferably administered orally, most preferably as a supplement to the animal's diet.

The following examples are given to further illustrate the present invention. The present invention is not limited to the specific details set forth in the examples.

EXAMPLE 1

Effects of Feeding Anti-PLA2 Antibody on Body Weight Uniformity

Materials and Methods

One-day old RossXRoss male chicks were randomly assigned to receive either an anti-$PLA_2$ antibody diet or a control diet. The chickens were housed 5 per pen, with 5 to 10 pens per treatment group in battery cages. The egg yolk anti-$PLA_2$ antibodies were produced as described below in Example 2. Egg yolk powder containing anti-$PLA_2$ antibodies was mixed into chick mash feed at a dose of 0.03% to 0.24% by weight. Feed and water were provided ad lib. Body weights were recorded on day 1 and day 22. A total of 16 independent trials were conducted and each trial had between 1 and 6 comparison groups (anti-$PLA_2$ antibody diet group and control diet group). Coefficient of variation was calculated for each control and anti-$PLA_2$ antibody group. Paired T test (one tail) was used to compare the coefficients of variation between the control and anti-$PLA_2$ antibody groups.

Results

As expected from the random assignment of chickens at the beginning of the trials, the coefficients of variation of the means of body weights are the same for the control and anti-$PLA_2$ antibody groups on day 1 (data not shown). The day 22 data as shown in Table 1 demonstrated that feeding chickens with an anti-$PLA_2$ antibody can reduce the coefficient of variation of the mean body weight and thus improve body weight uniformity.

TABLE 1

| Trial | CV*-Control group | CV*-$PLA_2$ antibody group | $PLA_2$ antibody yolk powder in diet (g/kg) |
|---|---|---|---|
| 1 | 8.473 | 8.26 | 1 |
| 2 | 7.281 | 3.353 | 0.5 |
| 2 | 7.281 | 6.036 | 1 |
| 3 | 16.766 | 10.921 | 0.5 |
| 3 | 16.766 | 9.354 | 1 |
| 4 | 14.88 | 11.39 | 1 |
| 5 | 12.163 | 2.825 | 0.5 |
| 5 | 12.163 | 14.131 | 1 |
| 5 | 12.163 | 14.548 | 1.5 |
| 5 | 12.163 | 10.942 | 0.5 |
| 5 | 12.163 | 10.568 | 1 |
| 5 | 12.163 | 8.716 | 1.5 |
| 6 | 20.63 | 22.39 | 0.5 |
| 6 | 20.63 | 15.18 | 1 |
| 6 | 20.63 | 29.85 | 0.5 |
| 6 | 20.63 | 12.77 | 1 |
| 7 | 7.51 | 11.148 | 0.3 |
| 7 | 7.51 | 9.92 | 0.6 |
| 8 | 8.528 | 11.616 | 0.6 |
| 8 | 8.528 | 8.842 | 0.6 |
| 9 | 5.255 | 6.75 | 0.4 |
| 9 | 5.255 | 11.53 | 0.8 |
| 10 | 7.194 | 6.17 | 0.4 |
| 10 | 7.194 | 5.549 | 0.8 |
| 11 | 9.1 | 7.768 | 0.6 |
| 11 | 9.1 | 7.373 | 0.6 |
| 12 | 9.796 | 9.624 | 1.2 |
| 12 | 9.796 | 8.086 | 2.4 |
| 13 | 11.043 | 6.607 | 1 |
| 13 | 11.043 | 8.484 | 1 |
| 13 | 11.043 | 9.928 | 1 |
| 14 | 5.938 | 10.296 | 1.2 |
| 14 | 5.938 | 5.692 | 2.4 |
| 15 | 9.857 | 11.059 | 1.2 |
| 15 | 9.857 | 6.708 | 1.2 |
| 16 | 10.564 | 10.61 | 1.5 |
| 16 | 10.564 | 8.31 | 1.5 |
| 16 | 10.564 | 12.593 | 1.5 |
| Mean | 11.00 | 10.16 | |

Pair T test P value 0.088
*Coefficient of variation.

EXAMPLE 2

Effects of Feeding Anti-$PLA_2$ Antibody on Carcass Yield

Materials and Methods

Egg yolk antibody production: Three hundred laying hens were injected with $PLA_2$ for egg yolk antibody production. Antigen was prepared by emulsifying equal volume of antigen solution (3 mg/ml) with Freund's adjuvant (Sigma, St. Louis, Mo.). Each hen was injected intramuscularly with a total of 1 ml emulsified $PLA_2$ (each of the two thighs and two breasts was injected with one 0.25 ml inoculum). Freund's complete adjuvant was used only in the first inoculation and Freund's incomplete adjuvant was used in the later injections. Second inoculation was one week after the first inoculation and the subsequent inoculations were two months apart.

Birds were checked daily for morbidity and mortality. Egg production was also recorded daily. Eggs from hens inoculated with $PLA_2$ were collected starting at day 21 after the first inoculation. Eggs were then broken and liquid eggs were mixed with an encapsulation compound and then spray-dried with a food grade dryer.

Broiler growth-out trial: The birds used in the trial were Cockerel broiler chicks obtained from Pine Manor (Goshen, Ind.). Chicks were brooded at four pens/treatment and 225 chicks/pen for the first 13 days (a total of 16 pens), after which the chicks were raised in a total of 28 pens (10'×15') with approximately 125 birds each. Chicks were fed 0.1%, 0.2% or 0.4% anti-$PLA_2$ egg antibody powder (with encapsulation material) or control mash diet for 45 days to get to market weight. Chicks were checked daily to remove dead chicks. Feed and water were provided ad lib. Feed weights were taken at the times when diets were changed and at the start and the end of the trial. Chicks were weighed weekly and processed at the end of the trial to get the carcass yield (carcass weight (without giblets, neck, fat pad) divided by animal weight immediately before slaughter). Data were analyzed by one-way ANOVA.

Results

As shown in Table 2 below, chicks fed a diet containing 0.1%, 0.2% or 0.4% anti-$PLA_2$ egg antibody powder had a higher carcass yield than chicks fed a control diet. The effect of anti-$PLA_2$ antibody is highly significant (p<0.0002). The linear regression analysis showed a highly significant linear relationship (p<0.0001) between the dose of anti-$PLA_2$ antibody and the increase in carcass yield. The overall SEM taking into account all control and treatment groups is 0.4%.

The total mortality rate of the trial is 3.3%. 4.7% of the chicks were also pulled from the trial as culls, which had compromised health and/or were likely to affect the performance of other chicks in the flock.

TABLE 2

|  | Control | 0.1% anti-PLA$_2$ egg antibody powder | 0.2% anti-PLA$_2$ egg antibody powder | 0.4% anti-PLA$_2$ egg antibody powder |
| --- | --- | --- | --- | --- |
| Carcass yield | 70.8% | 71.0% | 72.4% | 73.0% |

The present invention is not intended to be limited to the foregoing examples, but to encompass all such modifications and variations as come within the scope of the appended claims.

We claim:

1. A method for improving body weight uniformity in a target group of animals, the method comprising the step of administering orally to said target group of animals along with diet an egg yolk powder containing anti-phospholipase A$_2$ (anti-PLA$_2$) antibodies in an amount sufficient to improve body weight uniformity wherein the ratio of the egg yolk powder to the diet by weight is from 0.6 g/kg to 2.4 g/kg.

2. The method of claim 1, wherein the amount of anti-phospholipase A$_2$ (anti-PLA$_2$) antibody in the egg yolk powder administered orally along with diet is an amount sufficient to improve body weight uniformity by at least 0.5 as measured by a decrease in the coefficient of variation for body weights of the group of animals.

3. The method of claim 2, wherein the amount of anti-phospholipase A$_2$ (anti-PLA$_2$) antibody in the egg yolk powder administered orally along with diet is an amount sufficient to decrease the coefficient of variation by at least 0.8.

4. The method as claimed in claim 1, wherein the animals are selected from avians and mammals.

5. The method as claimed in claim 4, wherein the avians are selected from chickens, turkeys, ducks, pheasants, geese and quail.

6. The method as claimed in claim 4, wherein the mammals are selected from swine animals, bovine animals, ovine animals and caprine animals.

7. The method of claim 1, wherein the target group of animals is a group of chickens.

8. The method of claim 1, further comprising the step of measuring body weight uniformity in said target group of animals.

* * * * *

UNITED STATES PATENT AND TRADEMARK OFFICE
CERTIFICATE OF CORRECTION

PATENT NO. : 7,579,002 B2 Page 1 of 1
APPLICATION NO. : 10/761715
DATED : August 25, 2009
INVENTOR(S) : Mark E. Cook, Mingder Yang and Kevin Roberson It is certified that error appears in the above-identified patent and that said Letters Patent is hereby corrected as shown below:

Column 1, lines 14-17,

Please replace the Statement Regarding Federally Sponsored Research or Development with the following paragraph:

This invention was made with United States government support awarded by the following agencies:

USDA/CSREES 2002-34481-11930. The United States government has certain rights in this invention.

Signed and Sealed this

Twelfth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,579,002 B2 | Page 1 of 1 |
| APPLICATION NO. | : 10/761715 | |
| DATED | : August 25, 2009 | |
| INVENTOR(S) | : Cook et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 757 days.

Signed and Sealed this

Fourteenth Day of September, 2010

David J. Kappos
*Director of the United States Patent and Trademark Office*